(12) United States Patent  
Farley

(10) Patent No.: US 11,331,219 B2
(45) Date of Patent: May 17, 2022

(54) MULTIPLE ILLUMINATION TRANSMISSION THROUGH OPTICAL FIBER

(71) Applicant: Novartis AG, Basel (CH)

(72) Inventor: Mark Harrison Farley, Laguna Hills, CA (US)

(73) Assignee: Alcon Inc., Fribourg (CH)

( * ) Notice: Subject to any disclaimer, the term of this patent is extended or adjusted under 35 U.S.C. 154(b) by 502 days.

(21) Appl. No.: 16/220,599

(22) Filed: Dec. 14, 2018

(65) Prior Publication Data

US 2019/0209372 A1 Jul. 11, 2019

Related U.S. Application Data

(60) Provisional application No. 62/613,813, filed on Jan. 5, 2018.

(51) Int. Cl.
| | |
|---|---|
| *A61B 18/22* | (2006.01) |
| *A61F 9/008* | (2006.01) |
| *A61B 18/24* | (2006.01) |
| *A61B 3/14* | (2006.01) |
| *H04B 10/25* | (2013.01) |
| *H04J 14/08* | (2006.01) |

(52) U.S. Cl.
CPC ............ *A61F 9/0084* (2013.01); *A61B 3/145* (2013.01); *A61B 18/22* (2013.01); *A61B 18/24* (2013.01); *A61F 9/008* (2013.01); *H04B 10/25* (2013.01); *H04J 14/08* (2013.01); *A61F 2009/00863* (2013.01); *A61F 2009/00874* (2013.01)

(58) Field of Classification Search
None
See application file for complete search history.

(56) References Cited

U.S. PATENT DOCUMENTS

| | | |
|---|---|---|
| 5,651,783 A | 7/1997 | Raynard |
| 6,611,546 B1 | 8/2003 | Garnache |
| 8,398,240 B2 | 3/2013 | Smith |
| 8,914,098 B2 | 12/2014 | Brennan |
| 8,968,347 B2 | 3/2015 | McCollam |
| 8,992,021 B2 | 3/2015 | Smith |
| 9,956,053 B2 | 5/2018 | Diao |

(Continued)

FOREIGN PATENT DOCUMENTS

| | | |
|---|---|---|
| EP | 2298214 A2 | 3/2011 |
| WO | WO2014145465 A2 | 9/2014 |

*Primary Examiner* — Ankit D Tejani

(57) ABSTRACT

Provided herein is a probe for treating an eye of a patient. In one or more embodiments, the probe includes a body, and a tubular element having a main lumen extending from the body, the tubular element comprising a distal end. The probe further includes a visualization optical fiber within the main lumen, the visualization optical fiber adapted to emit an illumination provided by at least one of a plurality of light sources connected to the visualization optical fiber. In some embodiments, the probe further includes an optical switching system (e.g., a time-division multiplexor) operable with the plurality of light sources, wherein the optical switching system is adapted to independently control each of the plurality of light sources. By providing time-division multiplexing between different surgical light sources, quasi-simultaneous illumination delivery through the same optical path may be achieved.

19 Claims, 7 Drawing Sheets

(56) References Cited

U.S. PATENT DOCUMENTS

| | | |
|---|---|---|
| 10,016,248 B2 | 7/2018 | Mirsepassi |
| 10,238,543 B2 | 3/2019 | Farley |
| 10,307,290 B2 | 6/2019 | Kern |
| 10,322,028 B2 | 6/2019 | Price |
| 10,376,414 B2 | 8/2019 | Hallen |
| 10,405,886 B2 | 9/2019 | Washburn, II |
| 10,485,630 B2 | 11/2019 | Dos Santos |
| 2005/0171437 A1 | 8/2005 | Carberry |
| 2011/0279821 A1 | 11/2011 | Brennan |
| 2016/0035314 A1* | 2/2016 | Pan ................ G09G 3/2085 345/520 |
| 2016/0175149 A1* | 6/2016 | McDonell ........... A61F 9/00745 600/249 |
| 2017/0172792 A1* | 6/2017 | Mirsepassi ............ A61F 9/0008 |
| 2018/0055596 A1 | 3/2018 | Johnson |
| 2018/0132963 A1 | 5/2018 | Diao |
| 2018/0168861 A1* | 6/2018 | Mirsepassi .......... A61F 9/00736 |
| 2019/0201238 A1 | 7/2019 | Bacher |
| 2019/0282322 A1 | 9/2019 | Mirsepassi |

\* cited by examiner

MULTIPLE ILLUMINATION TRANSMISSION THROUGH OPTICAL FIBER

PRIORITY CLAIM

This application claims the benefit of priority of U.S. Provisional Patent Application Ser. No. 62/613,813 titled "MULTIPLE ILLUMINATION TRANSMISSION THROUGH OPTICAL FIBER," filed on Jan. 5, 2018, whose inventor is Mark Harrison Farley, which is hereby incorporated by reference in its entirety as though fully and completely set forth herein.

TECHNICAL FIELD

The present disclosure is directed to systems and instruments for use in medical procedures, and more particularly, to systems and instruments capable of illumination transmission.

BACKGROUND

Microsurgical instruments typically are used by surgeons for a variety of procedures. For example, in ophthalmic surgery, microsurgical instruments may be used for removal of tissue from delicate and restricted spaces. Microsurgical instruments may be used, for example, in procedures for removal of the vitreous body, blood, scar tissue, or the crystalline lens. Such instruments may include a control console and a surgical handpiece with which the surgeon dissects and removes the tissue. With respect to posterior segment surgery, the handpiece may be a vitreous cutter probe, a laser probe, an illumination probe, and/or an ultrasonic fragmenter for cutting or fragmenting the tissue. The handpiece may be connected to the control console by a long air-pressure (pneumatic) line and/or power cable, optical cable, or flexible tubes for supplying an infusion fluid to the surgical site and for withdrawing or aspirating fluid and cut/fragmented tissue from the site. The cutting, infusion, and aspiration functions of the handpiece may be controlled by the remote control console that provides power for the surgical handpiece(s) (e.g., a reciprocating or rotating cutting blade or an ultrasonically vibrated needle), and also controls the flow of infusion fluid and provides a source of vacuum (relative to atmosphere) for the aspiration of fluid and cut/fragmented tissue. The functions of the console may be controlled manually by the surgeon, usually by means of a foot-operated switch or proportional control.

Microsurgical instruments may also be used during vitreoretinal procedures, which are commonly performed within the posterior chamber of the human eye to treat various conditions of the posterior segment of the eye. In particular, vitreoretinal procedures may treat conditions such as age-related macular degeneration (AMD), diabetic retinopathy and diabetic vitreous hemorrhage, macular hole, retinal detachment, epiretinal membrane, cytomegalovirus (CMV) retinitis, and many other ophthalmic conditions.

Various configurations of prior art illuminated laser probes have been developed that utilize separate optical fibers for each light source and/or separate optical fibers for each coherent laser delivery. Some prior art surgical procedures utilize a first optical fiber for the delivery of non-coherent light for illumination and a second optical fiber, discrete and separate from the first optical fiber, for the delivery of coherent laser beam light for surgical treatment of tissues. In such configurations of probes, the group of illumination fibers are arranged side by side inside a common needle lumen. However, this prior art technology requires a larger incision, or more than one incision, to introduce multiple illumination sources and laser treatment lights into the eye or other structure, thereby generating greater trauma to the surgical site. Accordingly, it is desired to improve upon existing probes.

SUMMARY OF THE DISCLOSURE

One or more embodiments of the present disclosure may include a probe for treating an eye of a patient. The probe may include a body and a tubular element, such as a needle, having a main lumen extending from the body. The probe may further include a visualization optical fiber within the main lumen, the visualization optical fiber adapted to emit an illumination provided by at least one of a plurality of light sources operable with the visualization optical fiber.

One or more embodiments of the present disclosure may include a probe system including a probe, wherein the probe includes a body and a tubular element having a main lumen extending from the body. The tubular element may include a distal end. The probe may further include a single visualization optical fiber within the main lumen. The single visualization optical fiber may be adapted to emit an illumination from the distal end of the tubular element, the illumination provided by one of a plurality of light sources connected to the visualization optical fiber. The probe system may further include an optical switching system operable with the plurality of light sources. The optical switching system may be adapted to independently control each of the plurality of light sources.

One or more embodiments of the present disclosure may include an illumination method including connecting each of a plurality of light sources to a single visualization optical fiber. The illumination method may further include inserting a probe into an eye of a patient, wherein the probe includes a body, and a tubular element having a main lumen extending from the body. The tubular element may include a distal end inserted into the eye of the patient. The single visualization optical fiber may be located within the main lumen. The illumination method may further include emitting an illumination provided by one of the plurality of light sources connected to the single visualization optical fiber. An optical switching system operable with the plurality of light sources may permit switching between each of the plurality of light sources.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

Figure 1:
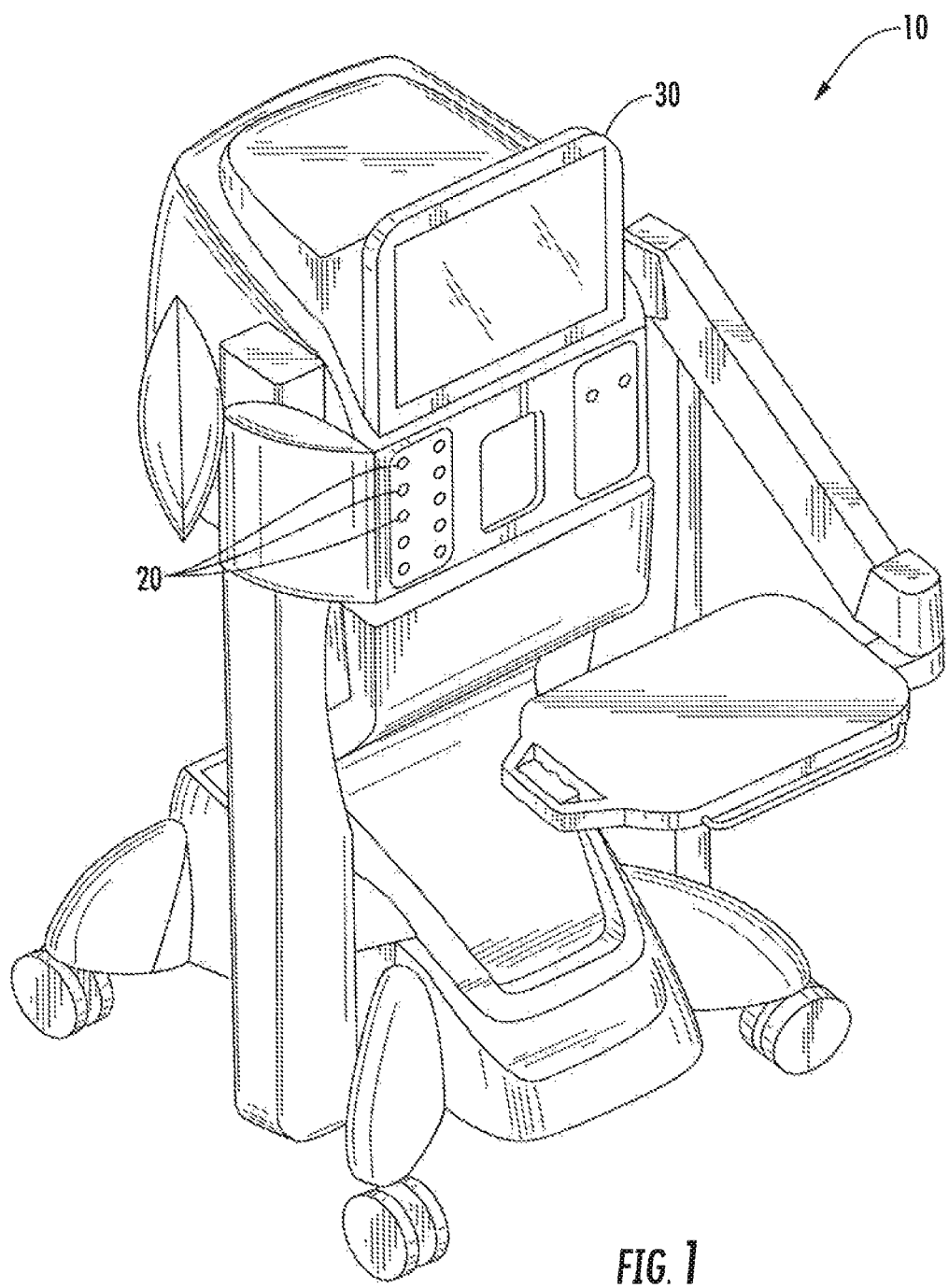
FIG. 1 illustrates a perspective view of an exemplary surgical system according to aspects of the present disclosure.

The accompanying drawings may be better understood by reference to the following detailed description.

DETAILED DESCRIPTION

For the purposes of promoting an understanding of the principles of the present disclosure, reference will now be made to the implementations illustrated in the drawings, and specific language will be used to describe the same. It will nevertheless be understood that no limitation of the scope of the disclosure is intended unless specifically indicated. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure. For simplicity, in some instances the same reference numbers are used throughout the drawings to refer to the same or like parts.

Ophthalmic surgical illumination devices for use with optical fibers have been manufactured by numerous companies for years. One such device is the Accurus® surgical system manufactured by Alcon Research Ltd., 6201 South Freeway, Fort Worth, Tex., 76134. The present disclosure improves on existing devices by permitting multiple illumination characteristics to be delivered through a single visualization/illumination optical fiber during ophthalmic surgery. Unlike prior art systems using one or more dedicated optical fibers to support each different light function or characteristic, embodiments herein advantageously permit combination, within a same optical fiber, of narrow and wide-angle beams of different intensities and wavelengths with independent modulation. By allowing multiple light sources to share the same optical fiber, a diameter of the needle can be reduced, thus minimizing trauma to the surgical site. Independent modulation of each of the multiplexed light sources can be achieved using a suitable method for each light source or combination of sources, such as time-length division multiplexing, wavelength division multiplexing, current/voltage control, polarization control, and/or optical attenuation.

As will be described in greater detail herein, embodiments of the present disclosure provide time-division multiplexing between different surgical light sources to achieve quasi-simultaneous delivery through the same optical path such as an optical fiber in a surgical instrument. Micro-electromechanical systems (MEMS) or other means of fast switching or modulation can be used to alternate between light sources. Switching frequencies above video and human refresh rates can provide the appearance of simultaneous lighting by multiple sources with different functions or characteristics. In the manner described herein, multiple light sources can be combined through one or more multiplexed optical switches in order to provide various illumination characteristics, e.g., to provide different colors, intensities, and divergence angles, which can be independently adjustable to provide visualization and illumination of various tissues or media, for example, during ophthalmic surgery.

Previously, multiple illumination characteristics have not been commonly used during ophthalmic surgery. Newer applications, such as vitreous visualization, have demonstrated the value of combining narrow and wide-angle beams of different intensities and wavelengths with independent modulation. Therefore, the embodiments herein provide an advantageous solution for vitreous visualization.

The present disclosure is broadly directed to systems and instruments for treating an eye of a patient. In one or more embodiments, the probe includes a body, and a tubular element such as a needle having a main lumen extending from the body, the tubular element comprising a distal end. The probe further includes a visualization optical fiber within the main lumen, the visualization optical fiber adapted for emitting an illumination provided by at least one of a plurality of light sources connected to the visualization optical fiber. In some embodiments, the probe further includes an optical switching system (e.g., a time-division multiplexor) operable with the plurality of light sources, wherein the optical switching system is adapted for independently controlling each of the plurality of light sources. By providing time-division multiplexing between different surgical light sources, quasi-simultaneous illumination delivery through the same optical path may be achieved.

FIG. 1 shows an example surgical console (interchangeably referred to as "console") 10 within the scope of the present disclosure. The surgical console may be a vitreoretinal surgical console, such as the Constellation® surgical console produced by Alcon Laboratories, Inc., 6201 South Freeway, Fort Worth, Tex., 76134. As shown, the console 10 may include one or more ports 20, which may be utilized for providing infusion and/or irrigation fluids to the eye or for aspirating materials from the eye. The console 10 may also include a display 30 for interfacing with the console 10, such as to establish or change one or more operations of the console 10. In some instances, the display 30 may include a touch-sensitive screen for interacting with the console 10 by touching the screen of the display 30. A probe, such as a vitrectomy probe including an illumination fiber connected to a plurality of lighting sources, may be coupled to a port 20 for dissecting ocular tissues and aspirating the ocular tissues from the eye.

Figure 2:
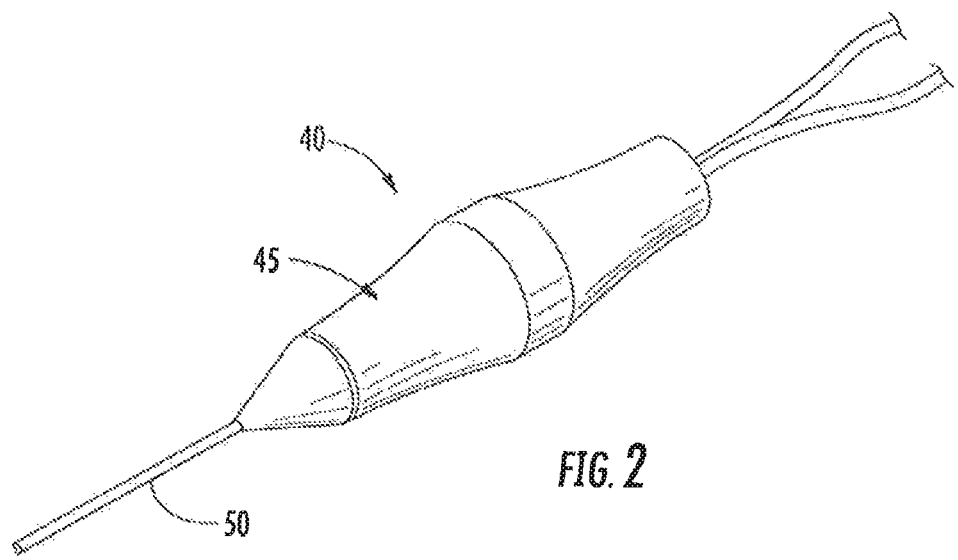
FIG. 2 illustrates a perspective view of an exemplary probe according to aspects of the present disclosure.
Figure 3:
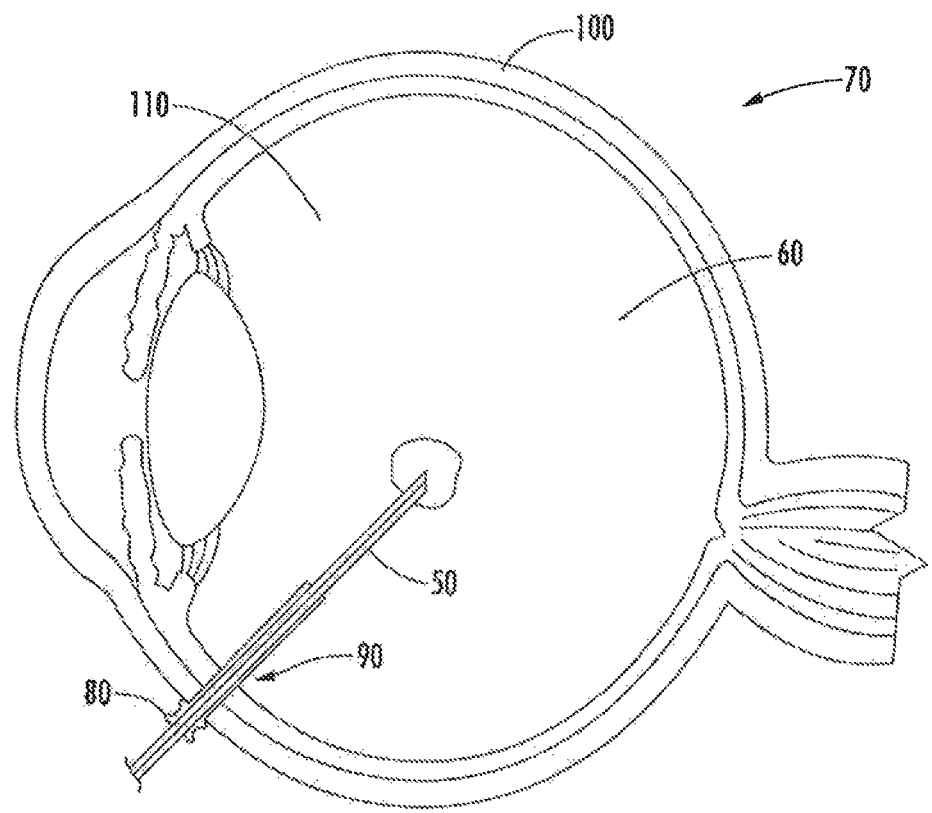
FIG. 3 is a cross-sectional illustration of an exemplary probe during use with a patient according to aspects of the present disclosure.

FIG. 2 shows an example vitrectomy probe 40 (hereinafter "probe"). The probe 40 includes a body 45 and a tubular element in the form of a needle 50 extending from the body 45. As illustrated in FIG. 3, during an ophthalmic surgical procedure, such as a retinal surgical procedure, the needle 50 may be inserted into the posterior segment 60 of the eye 70, such as through a cannula 80 disposed in an incision 90 through the sclera 100 of the eye 70, to illuminate, remove and/or aspirate ocular tissues. For example, during a retinal surgical procedure, the needle 50 may be inserted into the posterior segment 60 of the eye 70 to illuminate the surgical site within the eye 70 using one or more light sources. In some embodiments, the needle 50 may further include a cutter (e.g., mechanical or laser) to remove vitreous humor (interchangeably referred to herein as "vitreous" or "vitreous material") 110, a jelly-like substance that occupies the volume defined by the posterior segment 60. The needle 50 may also be used to remove membranes covering the retina or other tissues.

Figure 4:
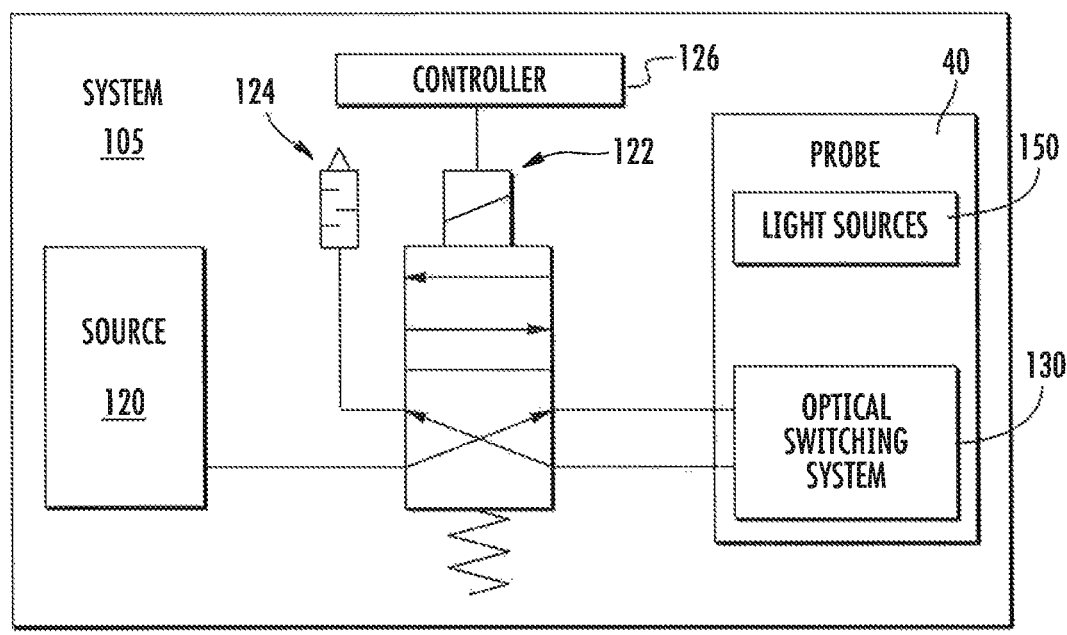
FIG. 4 is a block diagram of a probe system according to aspects of the present disclosure.

FIG. 4 is a schematic of exemplary components of a vitrectomy probe system 105. The vitrectomy probe system 105 may include the vitrectomy probe 40, a pneumatic pressure source 120, a probe driver shown as an adjustable directional on-off pneumatic driver 122, a muffler 124, and a controller 126. In an embodiment, the controller 126 may be a processor that includes one or more processing cores capable of performing parallel or sequential operations. Alternatively, the controller 126 may be a dedicated piece of hardware such as an application specific integrated circuit (ASIC), to name just a few examples. The pneumatic source 120, the driver 122, the muffler 124, and the probe 40 are in fluid communication with each other along lines representing flow paths or flow lines. The controller 126 is in electrical communication with the driver 122. In an embodiment, the controller 126 controls operation of both the driver 122 and various aspects of the probe 40. The vitrectomy probe system 105 may further include an optical switching system 130 operable with a plurality of light sources 150, as will be described in greater detail below.

Although not shown for the sake of brevity, the vitrectomy probe system 105 may include a number of subsystems that are used together to perform ocular surgical procedures, such as emulsification or vitrectomy surgical procedures. The vitrectomy probe system 105 may include an information or data storage system, which may include one or more types of memory, such as RAM (random-access memory), ROM (read-only memory), flash memory, a disk-based hard drive, and/or a solid-state hard drive. The controller 126 and data storage system may communicate over a bus, which may also permit communication with and between one or more of the plurality of subsystems of the vitrectomy probe system 105.

Figure 5:
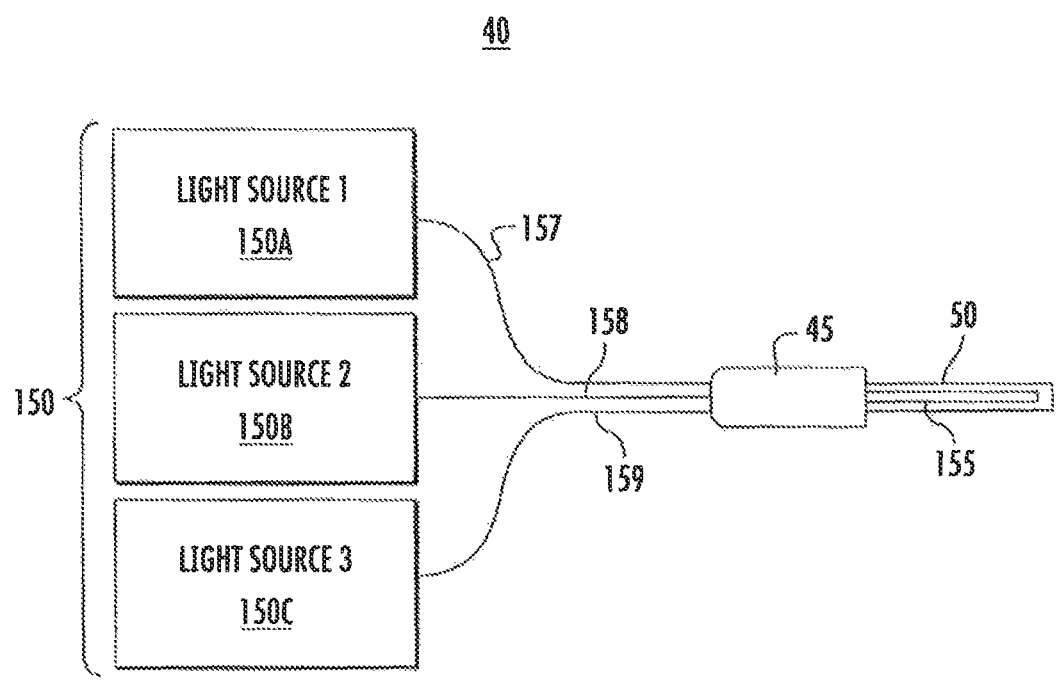
FIG. 5 is a stylized diagram showing a portion of the probe of FIG. 2, according to aspects of the present disclosure.

FIG. 5 is a diagram showing a portion of the illustrative vitrectomy probe 40 operable with the plurality of light sources 150. According to some embodiments, the vitrectomy probe 40 includes the plurality of light sources 150 connected to a handle or body 45 housing a visualization optical fiber 155 that terminates within the needle 50. The visualization optical fiber 155 may transmit light from one of the plurality of light sources 150A-C, which may provide, e.g., endoillumination for visualization, optical coherence tomography (OCT) imaging and/or biometry for visualization and diagnosis, for example, using a variety of illumination characteristics. In one non-limiting embodiment, the first light source 150A may be a narrow-angled beam connected to the visualization optical fiber 155 via connector 157, the second light source 150B may be a wide-angled beam connected to the visualization optical fiber 155 via connector 158, and the third light source 150C may be colored (e.g., blue or red) light connected to the visualization optical fiber 155 via connector 159. In various embodiments, each of the plurality of light sources 150 may have a different intensity (e.g., different wavelength). It will be appreciated that a greater or fewer number of light sources may be possible within the scope of the present disclosure.

Each of the connectors 157, 158, and 159 may be optical fibers, which are optically coupled into the single visualization optical fiber 155 within or before reaching the body 45 of the probe 40. For example, the optical coupling may be accomplished via use of one or more of, or a combination of, free-space optics, optical combiners, fused-fiber couplers, wavelength-division multiplexors, time length-division multiplexers, frequency-division multiplexors, or optical switches that alternate between each of the plurality of light sources 150A-C. In an exemplary embodiment, the output of each of the light sources 150A-C may be switched using MEMS or other means of fast switching or modulation to alternate between the plurality of light sources 150A-C. Switching frequencies above video and human eye refresh rates can be selected to provide the appearance of simultaneous lighting by multiple sources 150A-C, each with differing functions and/or characteristics.

In some embodiments, the body 45 forms a handle portion that may be grasped and manipulated by a surgeon when performing a surgical procedure, such as a vitrectomy. The body 45 may be made from a variety of materials commonly used to form such tools. For example, the body 45 may be made of a lightweight aluminum, a polymer, or other material. In various embodiments, the body 45 may be sterilized and used in more than one surgical procedure, or it may be a single-use device. The inner portion of the body 45 is designed to house the visualization optical fiber 155. In the embodiment shown, the plurality of light sources 150 are located external to the body 45. In other embodiments, one or more of the plurality of light sources 150 may be located within the body 45. Furthermore, the body 45 may house one or more switching components (e.g., MEMS or frequency-division multiplexor). In other embodiments, the switching component(s) may be located remote from the body 45.

In various embodiments, the probe 40 includes an endoillumination probe, which includes the visualization optical fiber 155 (e.g., a single-mode or multiple-mode optical fiber) connected to the plurality of light sources 150 (e.g., a halogen, mercury-vapor, xenon narrow or broad-spectrum bulbs, broadband, supercontinuum or narrow-band lasers, LEDs superluminescent diodes, laser diodes, or other solid state or semiconductor light emitting devices). The light provided by each of the plurality of light sources 150A-C travels through the visualization optical fiber 155 and illuminates a region of interest. Depending on the specific application, the free end or distal tip of the visualization optical fiber 155 may be terminated in any of a variety of ways. For example, the tip of the visualization optical fiber 155 may simply be polished and/or angled to provide specific areas and angles of illumination, or may couple to one or multiple lenses, e.g., for the purpose of focusing the light or causing it to diverge. In an alternate configuration, a lens is integrated into the visualization optical fiber 155 via gradient indexing, where the index of refraction of the fiber itself is gradually varied across the longitudinal axis of the visualization optical fiber 155 to provide convergence or divergence of the propagating light. Using a lens to disperse the light enables the use of a smaller-diameter fiber to achieve a similar area of illumination (spot size) at a given working distance, which is particularly useful in a multi or single-function probe in which a single visualization optical fiber is used.

Figure 6A:
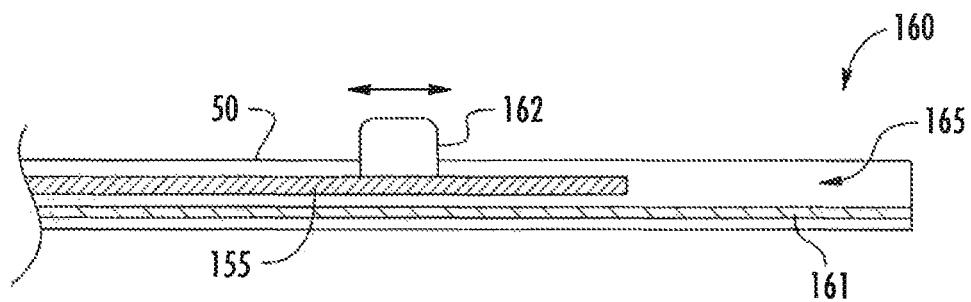
FIG. 6A is a side cross sectional view showing a portion of the probe of FIG. 2, according to aspects of the present disclosure.
Figure 6B:
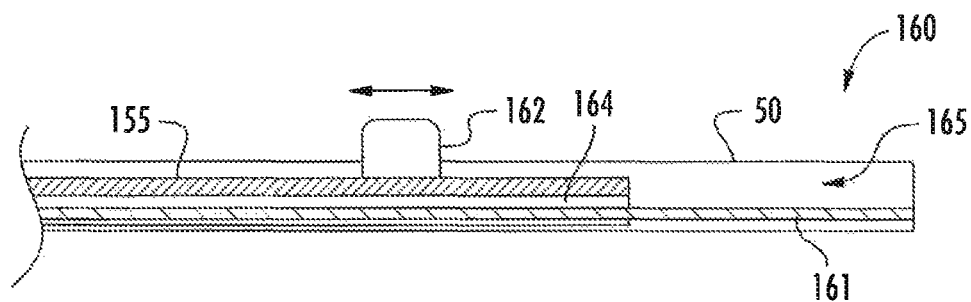
FIG. 6B is a side cross sectional view showing a portion of the probe of FIG. 2, according to aspects of the present disclosure.

Turning now to FIGS. 6A-B, the needle 50 of the probe 40 (FIG. 5) according to embodiments of the present disclosure will be described in greater detail. FIGS. 6A-B depict two different non-limiting fiber and lens configurations according to various embodiments of the disclosure. In the configuration shown in FIG. 6A, the probe tip 160 features the needle 50 containing a visualization optical fiber 155 and a treatment fiber 161. The visualization optical fiber 155 may be a multi-mode fiber for propagating endoillumination light to the distal end of probe tip 160. In some embodiments, the treatment fiber 161 may be an optical treatment fiber, such as a surgical laser fiber for projecting a laser beam out the probe tip 160. The end of the visualization optical fiber 155 is optionally recessed from the end of probe tip 160 in order to enable wider dispersion from the visualization optical fiber 155, resulting in a larger illuminating spot diameter for endoillumination. In some embodiments, the spot size may be adjusted through use of a slide lever 162 that is mechanically coupled to the visualization optical fiber 155. Movement of slide lever 162 along the longitudinal axis of the needle 50 adjusts the distance between the end of the visualization optical fiber 155 and the end of probe tip 160, resulting in different illumination spot sizes.

The configuration shown in FIG. 6B is similar to that of FIG. 6A, except both the visualization optical fiber 155 and the treatment fiber 161 are housed within an inner needle 164. In this example, the visualization optical fiber 155 is fixedly mounted within inner needle 164, causing the visualization optical fiber 155 to move with inner needle 164 when the slide lever 162 is repositioned. The treatment fiber 161 may thread through the inner needle 164, yet is attached to the needle 50 such that it does not move when the slide lever 162 is moved.

In some embodiments, the treatment fiber 161 may be designed to act as an optical waveguide and propagate a laser beam. In some examples, the characteristics of the laser beam propagated through the treatment fiber 161 are such that the laser beam causes disruption of vitreous fibrils within the path of the laser beam. In some embodiments, the laser may have a pulse rate within a range of about 10-500 kilohertz (kHz). This range can effectively provide disruption, which is the mechanical effect of light on tissue to disrupt or break down the tissue by laser-produced rapid ionization of molecules. Other ranges for characteristics of the laser beam that can provide disruption are contemplated as well.

In some examples, the probe 40 includes an aspiration lumen for aspirating the severed vitreous tissue and other vitreous fluids. The aspiration lumen may be in connection with a suction mechanism that provides a vacuum force to extract the severed tissue and other fluids. In some examples, a main lumen 165 of the needle 50 acts as part of the aspiration lumen, as illustrated. In some embodiments, however, a separate and independent cannula with an aspiration lumen is positioned within the main lumen 165. Such an aspiration lumen is in connection with a port of the needle so that severed tissue will appropriately pass into the aspiration lumen.

Figure 7:
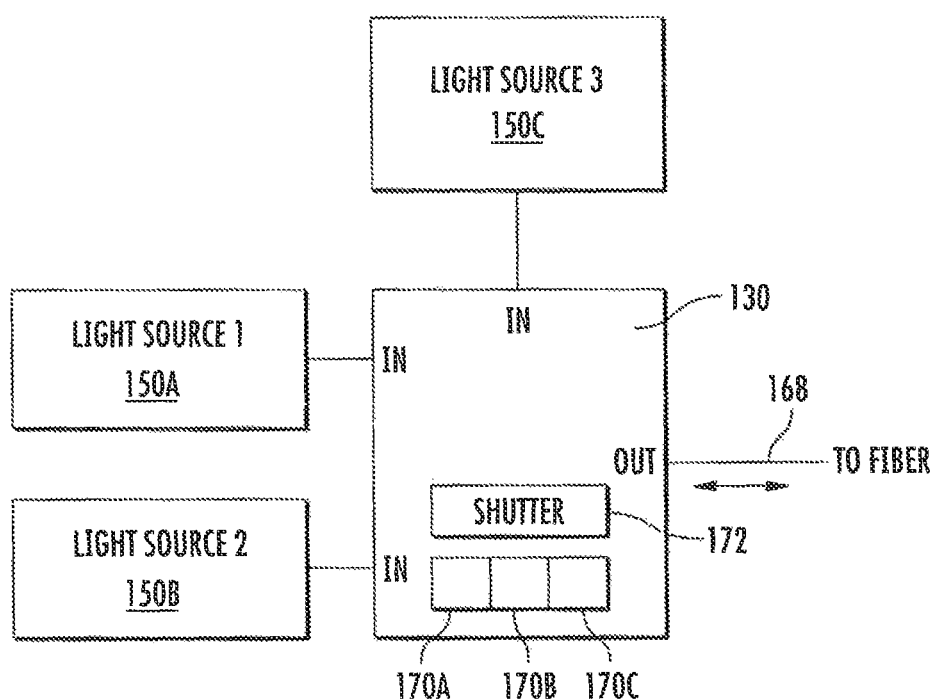
FIG. 7 is a block diagram illustrating an optical switching system according to aspects of the present disclosure.

Turning now to FIG. 7, operation of the optical switching system 130 according to some embodiments of the present disclosure will be described in greater detail. As shown, the optical switching system 130 is coupled to each of the plurality of light sources 150A-C, and includes an output 168 delivered to the visualization optical fiber 155. In some embodiments, the optical switching system 130 operates by selectively alternating between the light output of multiple constituent lasers having different wavelengths, e.g., in the red, green, and blue range, different luminous intensities, e.g., measured in candelas, and/or different divergences, e.g., narrow or wide-angle beams.

The optical switching system 130 may be an optical combiner, such as a time-division multiplexer. Time division multiplexing may be used for transmitting and routing signals in optical communication networks. In one example, time division multiplexing includes dividing up a frame, or window in time, into multiple evenly-spaced time slots, and synchronously inserting a single bit of data from lower-bandwidth sources (e.g., one or more of light sources 150A-C) into a higher-bandwidth multiplexed stream. Recovering the signal may include a demultiplexing operation in which the high-bandwidth stream is split into the individual low-bandwidth sources. The inherent simplicity of electronic time division multiplexing renders the processing logic and the devices required to be straightforward and more easily implemented than complex protocols.

In the embodiment shown in FIG. 7, the time-division multiplexing optical switching system 130 may include three (3) input signal optical fibers that transmit pulses to an array of corresponding optical switches 170A-C. Input pulses on the input fibers may be positioned in each corresponding time division multiplexing slot. In some embodiments, the multiplexing can be time-dithered to avoid temporal aliasing effects from the switching of the illumination when observed through optical or digital viewing systems. Furthermore, the multiplexing can serve as an efficient and reliable means of modulation and/or attenuation, potentially helping to decrease photic exposure or phototoxic injury to the tissue.

In some embodiments, the time-division multiplexing optical switching system 130 may include an optical shutter 172 to enable the light signals to be time-division multiplexed. In the illustrated example, the optical shutter 172 may be a rotatable wheel or disk, a digital light processing (DLP) device, a MEMS device, a rotating polygon mirror, a cascaded tunable optical filter or modulator, a liquid crystal diode shutter, and/or any other suitable optical shutter. In some examples, the plurality of light sources 150A-C may be controlled (e.g., switched periodically on and off) to convey the light signals in different time slots and/or at different frequencies, intensities, divergences, etc.

In other embodiments, the optical switching system 130 may be an optical time division multiplexor ("OTDM"). Some OTDMs include a fiber loop that contains a nonlinear optical element placed asymmetrically within the loop. The OTDM functions as an optical AND gate that allows an optical pulse to pass through when in the appropriate time slot. The OTDM operates by first splitting the input signal pulses into two beams which are coupled to the optical fiber loop but travel in opposite directions around the loop. An optical control pulse is timed to alter the index of refraction of the nonlinear optical element so that a phase difference is generated between the counter-propagating optical signal pulses. When the optical signal pulses traverse the fiber loop they are coupled back together. If the pulses are in phase, constructive interference occurs and the pulses can exit the OTDM. However, if the optical pulses are out of phase, deconstructive interference occurs and the optical signal cannot pass.

In an exemplary embodiment, the optical switching system 130 combines the light from the three light sources 150A-C into a single fiber-coupled output 168 suitable for interfacing to the probe 40 using a single-mode fiber. The optical switching system 130 is configured to independently control each of the plurality of light sources 150A-C to activate and deactivate each of the plurality of light sources 150A-C, e.g., according to a random switching frequency that is above a video refresh rate (e.g., 120, 240, or 300 frames per second) and a human eye refresh rate (e.g., approximately 50 Hz through 90 Hz) to alleviate synching artifacts or interference with other equipment.

The intensity of each wavelength of the plurality of light sources may be varied in order to alter each respective contribution to the endoillumination light output, e.g., to provide different therapeutic effects, provide improved visualization, or prevent tissue damage. This may enable a surgeon to view tissue under different hues of white light, which is useful in accentuating certain features, e.g., improving the contrast of certain structures (e.g., blood vessels) or stains, and/or causing stains to fluoresce (e.g., ophthalmic use of indocyanine green or tryptan blue). The intensity of contributing wavelengths may be adjusted to comply with safety guidelines such as those recommended by the International Commission on Non-Ionizing Radiation Protection to, for example, prevent photochemical retinal damage. In one non-limiting embodiment, the intensity of the blue contribution may be lowered in order to limit the blue spectral light from a white-light laser source. For example, light having wavelengths lower than approximately 475 nm may be filtered out of the output of white-light laser system in order to protect against phototoxicity. Such selected wavelengths may also be filtered out with an external filter coupled to the white-light laser source or probe.

Figure 8:
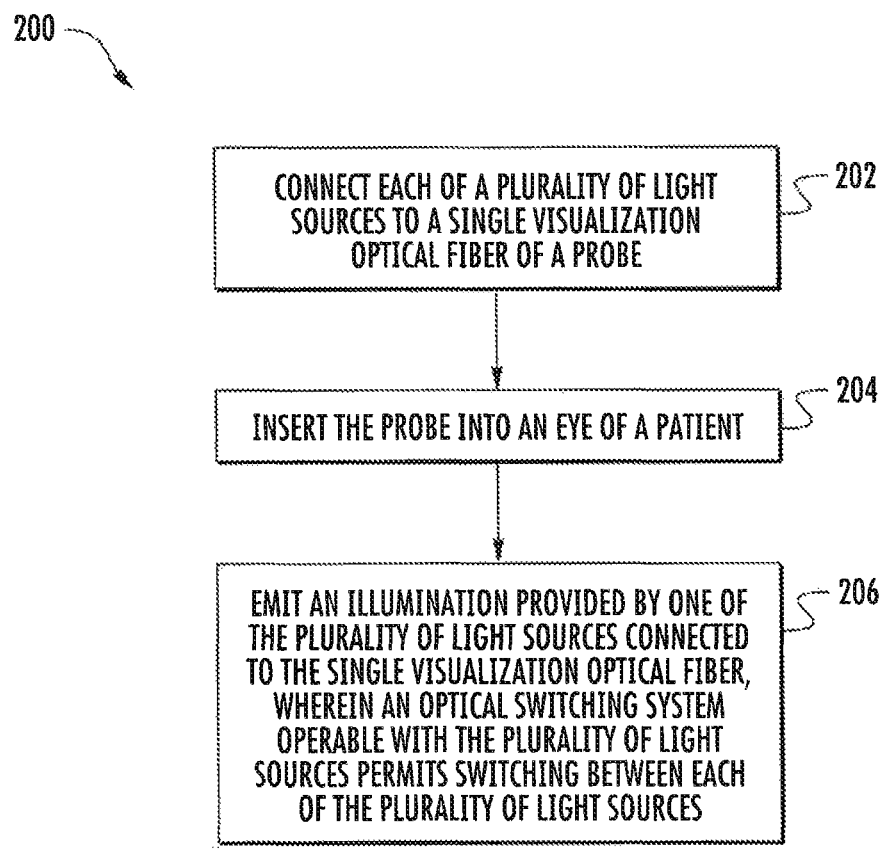
FIG. 8 is a flowchart showing an illustrative method for providing single fiber illumination according to aspects of the present disclosure.

FIG. 8 is a diagram illustrating a method 200 for treating a patient using a probe. As shown, at block 202 the method 200 may include connecting each of a plurality of light sources to a single visualization optical fiber of a probe. In some embodiments, each of the plurality of light sources includes a different illumination characteristic, such as color, wavelength, intensity, and/or divergence.

At block 204, the method 200 may include inserting the probe into an eye of a patient. In some embodiments, the probe is a vitrectomy probe. In some embodiments, the probe has a body, and a tubular element having a main lumen extending from the body, the tubular element comprising a distal end, which is inserted into the eye of the patient. The probe may further include a single visualization optical fiber within the main lumen.

At block 206, the method 200 may include emitting an illumination provided by one of the plurality of light sources connected to the single visualization optical fiber, wherein an optical switching system operable with the plurality of light sources permits switching between each of the plurality of light sources. In some embodiments, the method 200 may include switching between each of the plurality of light sources using a time-division multiplexor. In some embodiments, each of the plurality of light sources may be activated or deactivated each using a random switching frequency, wherein the random switching frequency is above a pre-determined video refresh rate to provide a perceived simultaneous illumination by two or more light sources of the plurality of light sources. However, during use, only one of the plurality of light sources is activated at a time to provide the illumination to the single visualization optical fiber.

Embodiments herein offer one or more of the following technical benefits/advantages. First, by allowing multiple light sources to share the same optical fiber, a diameter of the tubular element (e.g., needle) can be reduced, thus minimizing trauma to the surgical site. Second, time-division multiplexing between different surgical light sources may achieve quasi-simultaneous light delivery through the same optical path, even though only a single light source may be switched on at any given moment. Third, switching frequencies above video and human refresh rates may provide the appearance of simultaneous lighting by multiple sources, while alleviating synching artifacts or interference with other equipment.

Some embodiments may be described using the expressions "proximal" and "distal" when used in connection with a vitrectomy probe. As used herein, "proximal" refers to the end of the probe closest to the medical operator, whereas "distal" refers to the end of the probe inserted into a patient. Furthermore, as used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps, elements, and/or components, but do not preclude the presence or addition of one or more other features, regions, integers, steps, operations, elements, components, and/or groups thereof.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A vitrectomy probe system, the vitrectomy probe system comprising:
   a body;
   a tubular element having a main lumen extending from the body;
   a plurality of light sources connected to the body comprising a first light source with a narrow-angled beam and a second light source with a wide-angled beam;
   an optical switching system operable with the plurality of light sources, wherein the optical switching system is configured to switch between the plurality of light sources at a switch frequency; and
   a visualization optical fiber within the main lumen, the visualization optical fiber configured to emit an illumination provided by the plurality of light sources operable with the visualization optical fiber through the optical switching system;
   wherein the switch frequency of the switching between the plurality of light sources is above a human eye refresh rate to provide an appearance of simultaneous lighting by the plurality of light sources through the visualization optical fiber.

2. The vitrectomy probe system of claim 1, wherein the optical switching system independently controls each of the plurality of light sources.

3. The vitrectomy probe system of claim 1, wherein the optical switching system is a time-division multiplexor.

4. The vitrectomy probe system of claim 3, wherein the time-division multiplexor includes one or more microelectromechanical systems for switching between each of the plurality of light sources.

5. The vitrectomy probe system of claim 1, wherein the optical switching system activates and deactivates each of the plurality of light sources according to a random switching frequency.

6. The vitrectomy probe system of claim 5, wherein the random switching frequency is above a predetermined video refresh rate.

7. The vitrectomy probe system of claim 1, wherein each of the plurality of light sources comprises a different illumination characteristic.

8. The vitrectomy probe system of claim 7, wherein the illumination characteristic comprises at least one of the following: wavelength, intensity, and divergence.

9. The vitrectomy probe system of claim 1, further comprising an optical treatment fiber within the main lumen, the optical treatment fiber projecting a laser beam.

10. A vitrectomy probe system comprising:
a vitrectomy probe comprising:
a body;
a tubular element having a main lumen extending from the body, the tubular element comprising a distal end;
a plurality of light sources connected to the body comprising a first light source with a narrow-angled beam and a second light source with a wide-angled beam;
a single visualization optical fiber within the main lumen, the single visualization optical fiber configured to emit an illumination from the distal end of the tubular element, wherein the illumination is provided by the plurality of light sources connected to the single visualization optical fiber; and
an optical switching system operable with the plurality of light sources, the optical switching system configured to independently control each of the plurality of light sources and wherein the optical switching system is configured to switch between the plurality of light sources at a switch frequency;
wherein the switch frequency of the switching between the plurality of light sources is above a human eye refresh rate to provide an appearance of simultaneous lighting by the plurality of light sources through the visualization optical fiber.

11. The vitrectomy probe system of claim 10, wherein the optical switching system is a time-division multiplexor.

12. The vitrectomy probe system of claim 11, wherein the time-division multiplexor includes one or more microelectromechanical systems for switching between each of the plurality of light sources.

13. The vitrectomy probe system of claim 10, wherein the optical switching system activates or deactivates each of the plurality of light sources according to a random switching frequency.

14. The vitrectomy probe system of claim 10, wherein each of the plurality of light sources comprises a different illumination characteristic, the illumination characteristic comprising at least one of the following: wavelength, intensity, and divergence.

15. An illumination method comprising:
connecting each of a plurality of light sources to a single visualization optical fiber, wherein the plurality of light sources comprises a first light source with a narrow-angled beam and a second light source with a wide-angled beam;
inserting a vitrectomy probe into a patient, the vitrectomy probe comprising:
a body; and
a tubular element having a main lumen extending from the body, the tubular element comprising a distal end inserted into the patient, and
wherein the single visualization optical fiber is located within the main lumen; and
emitting an illumination provided by one of the plurality of light sources connected to the single visualization optical fiber, wherein an optical switching system operable with the plurality of light sources permits switching between each of the plurality of light sources at a switch frequency;
wherein the switch frequency of the switching between the plurality of light sources is above a human eye refresh rate to provide an appearance of simultaneous lighting by the plurality of light sources through the visualization optical fiber.

16. The illumination method of claim 15, further comprising switching between each of the plurality of light sources using a time-division multiplexor.

17. The illumination method of claim 15, further comprising activating or deactivating each of the plurality of light sources according to a random switching frequency, wherein the random switching frequency is above a predetermined video refresh rate to provide a perceived simultaneous illumination by two or more light sources of the plurality of light sources.

18. The illumination method of claim 15, wherein only one of the plurality of light sources is activated at a time to provide the illumination to the single visualization optical fiber.

19. The illumination method of claim 15, wherein each of the plurality of light sources comprises a different illumination characteristic, the illumination characteristic comprising at least one of the following: wavelength, intensity, and divergence.

* * * * *